(12) United States Patent
Hishikawa (10) Patent No.: US 9,555,266 B2
(45) Date of Patent: Jan. 31, 2017

(54) DEVICE FOR REMOTELY CROSS-FIRING PARTICLE BEAMS

(71) Applicant: MEDIPOLIS MEDICAL RESEARCH INSTITUTE, Ibusuki-shi, Kagoshima (JP)

(72) Inventor: Yoshio Hishikawa, Ibusuki (JP)

(73) Assignee: MEDIPOLIS MEDICAL RESEARCH INSTITUTE, Ibusuki-shi, Kagoshima (JP)

( * ) Notice: Subject to any disclaimer, the term of this patent is extended or adjusted under 35 U.S.C. 154(b) by 18 days.

(21) Appl. No.: 14/389,613

(22) PCT Filed: Mar. 27, 2013

(86) PCT No.: PCT/JP2013/059131
§ 371 (c)(1),
(2) Date: Sep. 30, 2014

(87) PCT Pub. No.: WO2013/146945
PCT Pub. Date: Oct. 3, 2013

(65) Prior Publication Data
US 2015/0328482 A1 Nov. 19, 2015

(30) Foreign Application Priority Data
Mar. 31, 2012 (JP) ................................. 2012-083422

(51) Int. Cl.
*A61N 5/10* (2006.01)
(52) U.S. Cl.
CPC .......... *A61N 5/1045* (2013.01); *A61N 5/1049* (2013.01); *A61N 5/1069* (2013.01); *A61N 5/1081* (2013.01);
(Continued)

(58) Field of Classification Search
CPC ............................ A61N 5/1045; A61N 5/1049
See application file for complete search history.

(56) References Cited

U.S. PATENT DOCUMENTS

2005/0029472 A1 2/2005 Ueno et al.
2008/0298553 A1* 12/2008 Takahashi ............ A61N 5/1042
378/152

(Continued)

FOREIGN PATENT DOCUMENTS

JP 2005-027681 A 2/2005
JP 2008-022994 A 2/2008

(Continued)

OTHER PUBLICATIONS

Tsukasa Watanabe et al., Telecobalt radiation therapy which composed of Rotatory Cross Section Radiograph and Rotatory Conformation Therapy Unit. Japan Radiological Society magazine, Oct. 25, 1963, 23(7) p. 841-p. 848

*Primary Examiner* — Christine Sung
(74) *Attorney, Agent, or Firm* — Novick, Kim & Lee, PLLC; Jae Youn Kim (57) ABSTRACT

Provided is a device for multi-portal irradiation of particle beams which makes it possible to carry out multi-portal irradiation by remote operation without an operator having to enter an irradiation room. This device for remotely multi-portal irradiation of particle beams includes an irradiation room and a control room. The irradiation room comprises an irradiation device for emitting a particle beam at an irradiation target, an irradiation control device for controlling the position and direction of the irradiation device, and a support stand for supporting the irradiation target. The control room, in turn, includes a control device and a remote operation controller. The control device controls the position and direction of the irradiation device by controlling the irradiation control device.

8 Claims, 3 Drawing Sheets (52) U.S. Cl.
CPC ...... *A61N 5/1084* (2013.01); *A61N 2005/1052* (2013.01); *A61N 2005/1061* (2013.01); *A61N 2005/1087* (2013.01); *A61N 2005/1094* (2013.01)

(56) References Cited

U.S. PATENT DOCUMENTS

| | | | |
|---|---|---|---|
| 2011/0257457 A1* | 10/2011 | Graf | A61N 5/1045 600/1 |
| 2012/0253096 A1 | 10/2012 | Teshigawara | |
| 2013/0072744 A1* | 3/2013 | Moskvin | A61N 5/1045 600/1 |

FOREIGN PATENT DOCUMENTS

| | | | |
|---|---|---|---|
| JP | 2009-089853 A | | 4/2009 |
| JP | 2009072287 A | * | 4/2009 |
| JP | 2010-240085 A | | 10/2010 |
| JP | 2012-045291 A | | 3/2012 |

* cited by examiner

DEVICE FOR REMOTELY CROSS-FIRING PARTICLE BEAMS

TECHNICAL FIELD

The present invention relates to a device for remotely multi-portal irradiation of particle beams.

BACKGROUND ART

For example, JP 2009-89853 A (Patent Literature 1) discloses a particle beam irradiation method. This publication discloses that multi-portal irradiation is performed in a case where a target site cannot be irradiated with a particle beam unless the particle beam goes through a normal organ (paragraph 0017 in this publication).

JP 2008-22994 A (Patent Literature 2) discloses a particle beam therapy system in which a particle beam irradiation section (irradiation room) and a diagnosis support section (control room) are disposed on the same floor. However, with this system, an operator needs to enter the irradiation room to adjust the particle beam irradiation section every time multi-portal irradiation is performed.

When multi-portal irradiation is performed, an operator moves a position of a particle beam emitting apparatus every time particle beam irradiation is performed (Rei Watanabe, Nobuo Ono, and Katsumi Nagai, Journal of Japan Radiological Society vol. 23 No. 7 pp. 33 to 40, Oct. 25, 1963: Non Patent Literature 1).

CITATION LIST

Patent Literature

Patent Literature 1: JP 2009-89853 A
Patent Literature 2: JP 2008-22994 A

Non Patent Literature

Non Patent Literature 1: Rei Watanabe, Nobuo Ono, and Katsumi Nagai, Journal of Japan Radiological Society vol. 23 No. 7 pp. 33 to 40, Oct. 25, 1963

SUMMARY OF INVENTION

Technical Problem

When an operator enters an irradiation room to adjust an irradiation direction of a particle beam every time particle beam irradiation is performed as in the case of the multi-portal irradiation of the related art, there has been such a problem that it takes time for particle beam treatment.

An object of the present invention is to provide a device for multi-portal irradiation of particle beams making it possible to carry out multi-portal irradiation by remote operation without an operator having to enter an irradiation room.

An object of the present invention is to provide a device for multi-portal irradiation of particle beams capable of quickly performing multi-portal irradiation of particle beams.

Solution to Problem

Basically, the present invention has been made based on the finding that remotely multi-portal irradiation of particle beams can be performed by remotely controlling a particle beam irradiation device from a separate room from an irradiation room.

A device for remotely multi-portal irradiation of particle beams of the present invention includes an irradiation room 15 and a control room 21. The irradiation room includes an irradiation device 12 that emits a particle beam to an irradiation target 11, an irradiation control device 13 that controls a position and direction of the irradiation device 12, and a support stand 14 that supports the irradiation target 11. The irradiation room 15 may include an operation controller 17 that drives the irradiation control device 13 in its vicinity, as in a particle beam irradiation device of the related art. The device for remotely multi-portal irradiation of particle beams of the present invention includes an MLC remote monitoring camera 18 for checking a shape of a patient collimator (multileaf collimator; hereinafter abbreviated as MLC). On the other hand, the control room 21 includes a control device 22. Preferably, the control room 21 further includes a display section 42. Preferably, the control device 22 includes a remote operation controller 41 having a function equivalent to that of the controller of the irradiation control device 13 in the irradiation room 15. The control device 22 and the remote operation desktop controller 41 control the irradiation control device 13 to control the position and direction of the irradiation device 12.

In the device for remotely multi-portal irradiation of particle beams, preferably, the control device 22 stores information related to an irradiation field of the particle beam with which the irradiation target 11 is irradiated from each position and direction of the irradiation device 12 controlled by the irradiation control device 13. Thus, in the device for remotely multi-portal irradiation of particle beams, it is possible to irradiate the irradiation target with an adequate dose of the particle beam even when the irradiation device irradiates the irradiation target with the particle beam from a plurality of positions and directions. Furthermore, when the device for remotely multi-portal irradiation of particle beams has the remote operation controller 41, it is possible to control the irradiation control device 13 by the same operation as that of the operation controller 17 present in the vicinity of a irradiation control device 13 of the related art.

Preferably, the device for remotely multi-portal irradiation of particle beams further includes an imaging device 31 that detects and images a positron which is generated from the irradiation target when it is irradiated with the particle beam emitted from the irradiation device 12.

Preferably, the device for remotely multi-portal irradiation of particle beams further includes an X-ray photographing device 32 that performs X-ray photographing of the irradiation target.

Advantageous Effects of Invention

In the related art, upon the multi-filed irradiation, an operator enters the irradiation room to control the irradiation device every time the particle beam irradiation is performed. However, according to the present invention, by remotely controlling the particle beam, it is possible to reduce a treatment time, and significantly reduce burdens on a patient.

DESCRIPTION OF EMBODIMENTS

The present invention relates to a device for remotely multi-portal irradiation of particle beams. A particle beam irradiation device is a medical device that irradiates an affected part such as a tumor or a cancer with a charged particle beam (hereinafter, referred to as a "particle beam") typified by a heavy particle beam such as a carbon ion beam and a proton beam to perform treatment. A device for remotely multi-portal irradiation of particle beams is a device that irradiates an affected part with a particle beam adjusted in intensity or the like from multiple directions to treat the affected part with an adequate dose and reduce exposure of surrounding tissue. Note that, to irradiate an irradiation target such as an affected part with a particle beam from multiple directions is referred to as multi-portal irradiation of particle beams. The device for remotely multi-portal irradiation of particle beams means, in the context of the device for multi-portal irradiation of particle beams, a device that controls an irradiation direction and the like of the particle beam from outside the irradiation room.

Figure 1:
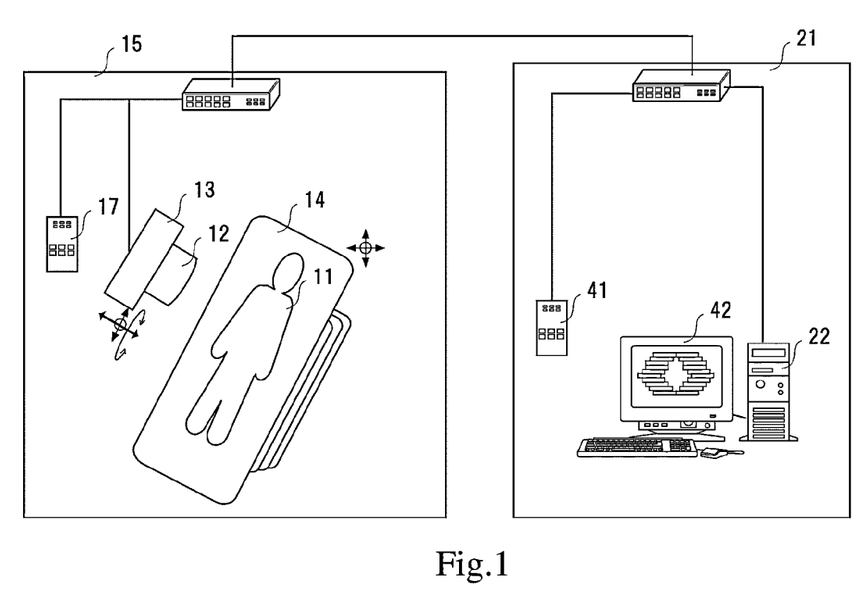
FIG. 1 is a conceptual view for explaining a device for remotely multi-portal irradiation of particle beams of the present invention.

FIG. 1 is a conceptual view for explaining a device for remotely multi-portal irradiation of particle beams of the present invention. As illustrated in FIG. 1, the device for remotely multi-portal irradiation of particle beams of the present invention includes an irradiation room 15 and a control room 21. The irradiation room 15 is also called a treatment room, and is a room where an irradiation target such as a patient is irradiated with a particle beam to treat a tumor or the like. On the other hand, the control room 21 is a room present in a separate space from the irradiation room 15 and is a room having a controller for controlling an irradiation system and a drive system in the irradiation room 15.

The irradiation room 15 includes an irradiation device 12 that emits the particle beam to an irradiation target 11, an irradiation control device 13 that controls a position and direction of the irradiation device 12, and a support stand 14 that supports the irradiation target 11.

The irradiation device 12 is an apparatus for emitting the particle beam. The particle beam is, for example, a charged particle beam typified by a heavy particle beam such as a carbon ion beam and a proton beam. Since the particle beam irradiation device has already been known (for example, see Patent Literatures 1 and 2, and Non Patent Literature 1), a known irradiation device can appropriately be used in the present invention. The irradiation device 12 includes any or all of a wobbler electromagnet, a scatterer, a ridge filter, a block collimator, a multileaf collimator, and a bolus. The wobbler electromagnet is an electromagnet that rotates the particle beam by a rotating magnetic field to flatten an irradiation field. It is preferable that drive of the wobble electromagnet can be controlled by a controller to be described later. The scatterer is an element for further scattering the particle beam spread by the wobbler electromagnet. The ridge filter is an element for changing a width or depth direction of Bragg peak of the particle beam in accordance with a treatment thickness of, e.g., a cancer. The block collimator is an element for blocking the particle beam outside a necessary range. The multileaf collimator, also called a patient collimator, is an element having a plurality of movable leaves to match the particle beam to a shape of, e.g., a cancer. The bolus is an element for adjusting a range of the particle beam in accordance with a shape of, e.g., a cancer. The multileaf collimator and bolus portion may be provided inside a localizing cone called a snout. The multileaf collimator (patient collimator) fitted inside the snout forms a shape in a lateral direction (cross-sectional direction) of an affected part as viewed from the beam. Then, the bolus fitted inside the snout, i.e., an energy absorbing body partially different in thickness performs adjustment such that the particle beam stops at a depth corresponding to a shape of a bottom of the affected part. The number of irradiation devices 12 may be one or more (e.g., two or more and 10 or less). When the plurality of irradiation devices 12 is present, the particle beam irradiation may less frequently be performed on the irradiation target, and thus a treatment time can be reduced.

The irradiation control device 13 is a device for controlling a position and direction of the irradiation device 12. For example, the irradiation control device 13 includes a holding section that holds the irradiation device 12, a position control section that controls a spatial position of the holding section, and a direction control section that controls a direction of the holding section. For example, the irradiation device 12 and the irradiation control device 13 are incorporated in a rotating gantry 51, or constitute a part of the rotating gantry 51. That is, the irradiation device of the present invention is, for example, preferably a rotating gantry irradiation device having the rotating gantry 51 capable of arbitrarily setting an irradiation direction. The irradiation device of the present invention may also be a fixed irradiation device in which the irradiation direction is fixed.

The support stand 14 is an element for supporting the irradiation target 11. For example, the support stand 14 is a bed on which a patient lies. Preferably, the support stand 14 is provided with an actuator and can move up and down, right and left, and fore and back based on a command from the controller or the like.

The irradiation room 15 may include an operation controller 17 for operating the irradiation control device 13. The operation controller 17 may be one that is present in a particle beam irradiation device of the related art. By using the operation controller 17, the irradiation control device 13 can be adjusted and a patient, which is the irradiation target, can adequately be irradiated with the particle beam. When the particle beam irradiation is remotely operated, the operation controller 17 may not be used. Furthermore, the operation controller 17 may be used only when a medical staff adjusts the particle beam irradiation device in order to perform the particle beam irradiation for the first time. Preferably, the operation controller 17 is a controller that receives an input of information through a button and the like, or a controller configured to be capable of receiving an input of information through a touch panel.

The irradiation room 15 has an MLC remote monitoring camera 18. In this case, the irradiation device 12 has a multileaf collimator (MLC). The multileaf collimator has a function of adjusting a shape of the particle beam with which a patient is irradiated. Preferably, when the position or direction (angle) of the irradiation device 21 is changed, a shape of the multileaf collimator is adjusted such that only a target site can be exposed to the particle beam while preventing a normal organ from being irradiated with the particle beam as much as possible. In a preferred aspect of the present invention, the shape of the multileaf collimator in the irradiation device 12 is photographed by the MLC remote monitoring camera 18 and displayed on a display section 42 in the control room, so that it is possible for an operator in the control room to control the irradiation device while checking the shape of the multileaf collimator. Note that the control device 22 may previously store information related to the shape of the multileaf collimator in accordance with the position and angle of the irradiation device 12. In this case, the control device 22 may issue a command to the irradiation control device 13 or the irradiation device 12 so as to adjust the shape of the multileaf collimator according to a change in the position and direction of the irradiation device 12. The shape of the multileaf collimator in the irradiation device 12 can be photographed by the MLC remote monitoring camera 18 and displayed on the display section 42 in the control room 21, thereby allowing an operator to check the shape of the multileaf collimator.

Figure 2:
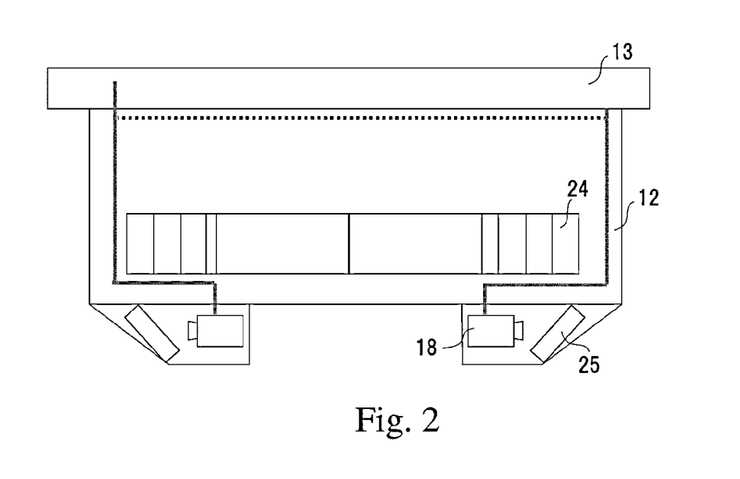
FIG. 2 is a conceptual view illustrating a configuration example of an MLC remote monitoring camera and an irradiation device.

FIG. 2 is a conceptual view illustrating a configuration example of the MLC remote monitoring camera and the irradiation device. As illustrated in FIG. 2, the shape of the multileaf collimator 24 included in the irradiation device is photographed through a mirror 25 by the MLC remote monitoring camera 18. The image photographed by the MLC remote monitoring camera 18 is processed by the control device 22 in the control room 21 into information capable of being displayed on the display 42.

Figure 3:
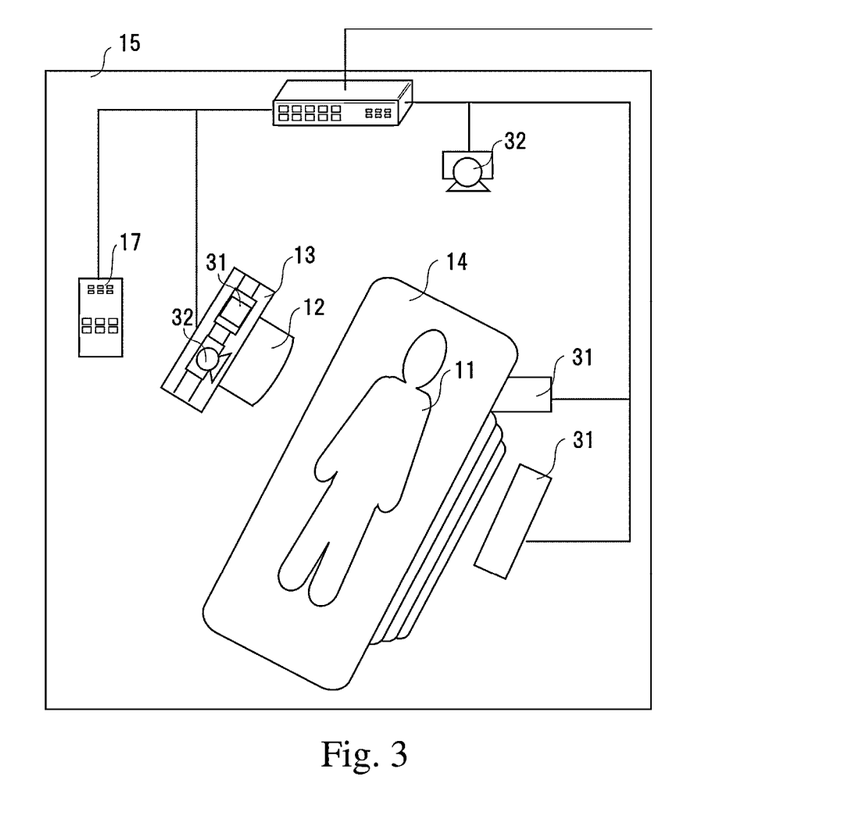
FIG. 3 is a conceptual view illustrating a particle beam irradiation device having an imaging device and an X-ray photographing device.

FIG. 3 is a conceptual view illustrating the particle beam irradiation device having an imaging device and an X-ray photographing device. As illustrated in FIG. 3, the irradiation room 15 may further be provided with an imaging device 31. The imaging device 31 is a device for detecting and imaging a positron which is generated from the irradiation target when it is irradiated with the particle beam emitted from the irradiation device 12 (see Patent Literature 2). The imaging device 31 is also called a PET diagnosis support section or a monitoring device. The PET diagnosis support section includes a scintillator array that takes out, as an electrical (detection) signal, a photon generated in response to a gamma-ray generated by pair-annihilation of a positron of a positron emitter produced by auto-activation in a body of the patient irradiated with a proton beam by a particle beam (proton beam) irradiation section, and a positron annihilation gamma-ray measurement section that indirectly measures the gamma-ray by taking up the electrical signal output from the scintillator array in synchronization with the proton beam irradiation. By combining the imaging device 31 with an X-ray CT apparatus or an MRI image diagnostic apparatus, real-time monitoring during particle beam irradiation treatment can be achieved, thereby enhancing diagnostic accuracy or improving treatment, which in turn can increase assurance and safety of medical services.

As illustrated in FIG. 3, the device for remotely multi-portal irradiation of particle beams may further include an X-ray photographing device 32 that performs X-ray photographing of the irradiation target. For example, the X-ray photographing device 32 is used for bed positioning. The bed positioning generally refers to a process of comparing a DRR (Digital Reconstructed Radiograph) image output from a treatment planning apparatus and an X-ray image (DR (Digital Radiograph) image) obtained by photographing, using the X-ray photographing device, a patient lying on the support stand (hereinafter, bed) before particle beam irradiation for treatment; calculating a deviation between a position of the irradiation target determined at the time of treatment planning and a current position of the irradiation target on the bed; obtaining a moving amount of the bed; and positioning the bed (patient). The X-ray photographing device performs X-ray photographing of the current irradiation target on the bed at the time of such bed positioning. The X-ray image photographing device includes an X-ray generator (X-ray source) and an X-ray receiver that receives an X-ray emitted from the X-ray generator. The X-ray receiver is disposed at a position facing the X-ray generator so as to receive the X-ray emitted from the X-ray generator. The bed is located between the X-ray generator and the X-ray receiver.

The control room 21 is a room present in a separate space from the irradiation room 15. The control room 21 and the irradiation room 15 may be present on different floors or may be present on the same floor. The control room 21 has the control device 22 (and the remote operation controller 41). For example, the control device 22 is a computer. The computer has an input/output section, an arithmetic section, a control section, and a storage section. The above elements are connected to each other through a bus or the like so as to allow information to be exchanged therebetween. The control device 22 and the remote operation controller 41 control the irradiation control device 13 to control the position and direction of the irradiation device 12. The controller 22 and the remote operation controller 41 may control a particle beam irradiation amount of the irradiation device 12. The control device 22 may control the above-described imaging device 31 and X-ray photographing device 32. The remote operation controller 41 may function as the control device 22. Furthermore, the display section may be configured as a touch panel and the touch panel may function as the control device 22.

In the device for remotely multi-portal irradiation of particle beams, preferably, the control device 22 stores information related to an irradiation field of the particle beam with which the irradiation target 11 is irradiated from each position and direction of the irradiation device 12 controlled by the irradiation control device 13. Thus, in the device for remotely multi-portal irradiation of particle beams, it is possible to irradiate the irradiation target with an adequate dose of the particle beam even when the irradiation device irradiates the irradiation target with the particle beam from a plurality of positions and directions. Furthermore, when the device for remotely multi-portal irradiation of particle beams has the remote operation controller 41, it is possible to control the irradiation control device 13 by the same operation as that of the operation controller 17 present in the vicinity of a irradiation control device 13 of the related art. The control room 21 may include the display section 42. The display section 42 is connected to, e.g., the control device 22. Then, the image of the multileaf controller photographed by the MLC remote monitoring camera 18 may appropriately be displayed on the display section 42 through the control device 22.

Next, an example of a treatment method using the device for remotely multi-portal irradiation of particle beams of the present invention will be described. In the following example, a treatment method using one irradiation device 12 will be described. However, two or more irradiation devices 12 may be present.

First, a patient enters the irradiation room 15. Then, a medical staff fixes the patient to the support stand 14. Thereafter, the medical staff moves the support stand 14 to carry out a rough positioning of the patient. The rough positioning of the patient is performed. The medical staff sets the X-ray photographing device. That is, the X-ray generator and the X-ray receiver are moved such that the X-ray generator and the X-ray receiver are at positions facing each other and that an affected part of the patient on the support stand 14 is located on a line connecting the X-ray generator and the X-ray receiver.

The medical staff inputs an X-ray photographing start signal from an X-ray control console. The X-ray photographing device having received the X-ray photographing start signal starts X-ray emission from the X-ray generator. The X-ray emitted from the X-ray generator and then passing through the patient's affected part is received by the X-ray receiver, and thereby X-ray photographing from the front or side of the patient's affected part is performed. After acquisition of X-ray image data necessary for creating an X-ray image, the X-ray emission from the X-ray generator is stopped.

The above-described step can be omitted in the absence of the X-ray generator.

The medical staff checks the position of the patient in the irradiation room 15. The X-ray receiver outputs the received X-ray image data to a positioning support system. The positioning support system creates a current image of the patient's affected part from the received X-ray image data and displays the current image on a display. Furthermore, the positioning support system reads a patient's treatment planning image that has previously been received from the treatment planning apparatus and stored in a storage device, and displays the patient's treatment planning image on the display. The positioning support system compares the current image and the treatment planning image displayed on the display, and determines whether or not there is a deviation between a current position of the irradiation target on the support stand 14 and the position of the irradiation target determined at the time of treatment planning (whether or not the deviation falls within a predetermined allowable range). When it is determined that there is the deviation between the current position of the irradiation target and the position of the irradiation target at the time of treatment planning (the deviation falls outside the allowable range), a positioning operator or the positioning support system obtains, based on the deviation amount in the position of the irradiation target, a moving amount of the support stand 14 in order to make the positions of the irradiation target coincide with each other (makes the deviation fall within the allowable range). A support stand controller (not illustrated) receives a support stand moving amount from the positioning support system and then moves, based on the support stand moving amount, the support stand 14 to perform fine adjustment of the patient position. After stop of the support stand 14, as needed, the medical staff inputs the X-ray photographing start signal from the X-ray control console, carries out the X-ray photographing again, and checks the position. When the positioning support system determines that the current position of the irradiation target on the support stand 14 and the position of the irradiation target determined at the time of treatment planning coincide with each other (when it is determined that the deviation falls within the predetermined allowable range and that the positions of the irradiation target coincide with each other), the X-ray photographing is ended, and the bed positioning is ended.

The medical staff starts preparation for the particle beam irradiation. Specifically, a patient collimator (multileaf collimator) corresponding to the patient lying on the support stand 14 is installed on a beam orbit in the irradiation device 12. Thereafter, the rotating gantry 51 is rotated by a predetermined rotating angle corresponding to a first field to install the snout at a predetermined position. Thereafter, the medical staff returns to the control room 21 and checks that the preparation for the particle beam irradiation is completed and that there is not any person (e.g., another medical staff, or another patient) other than the patient lying on the support stand 14 in the irradiation room 15. After the check, the medical staff inputs a particle beam irradiation start signal from the control device 22 in the control room. Upon output of the particle beam irradiation start signal to the particle beam irradiation device, the particle beam irradiation by the irradiation device 12 is started to start treatment. The installation of the rotating gantry 51 corresponding to the first field can also be performed automatically outside the irradiation room 15 (i.e., from the control room 21).

The control device 22 stores information related to an irradiation field of the particle beam with which the irradiation target 11 is irradiated from each position and direction of the irradiation device 12 controlled by the irradiation control device 13. For example, the control device 22 reads out, from the storage section, a first position and angle of the irradiation device 12, and control information of the irradiation device 12. The control information of the irradiation device 12 may include information related to intensity of the particle beam to be output from the irradiation device 12, as well as, for example, control information of the bolus and control information of the collimator. The control device 22 outputs a command to the irradiation control device 13 to control the position and direction of the irradiation device 12. Then, the irradiation control device 13 having received the command from the control device 22 changes a position of the holding section holding the irradiation device 12 to the first position and also adjusts the angle of the irradiation device 12 to the first angle. On the other hand, the control device 22 outputs a control command to the irradiation device 12. Then, based on the control command from the control device 22, the irradiation device 12 appropriately adjusts each element in the irradiation device 12, and then irradiates the irradiation target with the particle beam for a predetermined time.

The imaging device 31 detects and images a positron which is generated from the irradiation target when it is irradiated with the particle beam emitted from the irradiation device 12. The imaging device 31 is configured to be capable of outputting an imaging result to a monitor (display) in the control room. Thus, the medical staff in the control room can observe situations of the particle beam irradiation in real time.

Similarly, when the irradiation device is set to a second position and a second angle, a third position and a third angle, and subsequent positions and angles, the irradiation control device 13 adjusts the position and angle of the irradiation device according to the commands from the control device 22 and the remote operation controller 41, and the irradiation device 12 irradiates the irradiation target with the particle beam for a predetermined time.

After the end of the first-field irradiation, a rotating angle corresponding to a second filed is set using the remote operation controller 41 of the control room 21, and the rotating gantry 51 is moved to install the snout. Thereafter, the patient collimator (multileaf collimator) is installed in a shape corresponding to the second field, and the shape of the multileaf collimator is checked using the MLC remote monitoring camera 18. Thereafter, the medical staff inputs the particle beam irradiation start signal from the controller in the control room. Upon output of the particle beam irradiation start signal to the particle beam irradiation device, the particle beam irradiation by the irradiation device 12 is started to start second-field treatment. In the case of multi-field of the third field or more, the above operation is repeated similarly.

Thus, in the device for remotely multi-portal irradiation of particle beams, it is possible to irradiate the irradiation target with an adequate dose of the particle beam even when the irradiation device irradiates the irradiation target with the particle beam from a plurality of positions and directions.

As described above, in a preferred aspect of the present invention, the device for remotely multi-portal irradiation of particle beams includes the plurality of irradiation devices 12 and the irradiation target is irradiated with the particle beam from multiple directions at a time. Also in this case, the irradiation control device 13 that controls each irradiation device based on the control commands from the control device 22 and the remote operation controller 41 may adjust the position and angle of each irradiation device, and each irradiation device 12 may irradiate the irradiation target with the particle beam for a predetermined time.

Example 1

Figure 4:
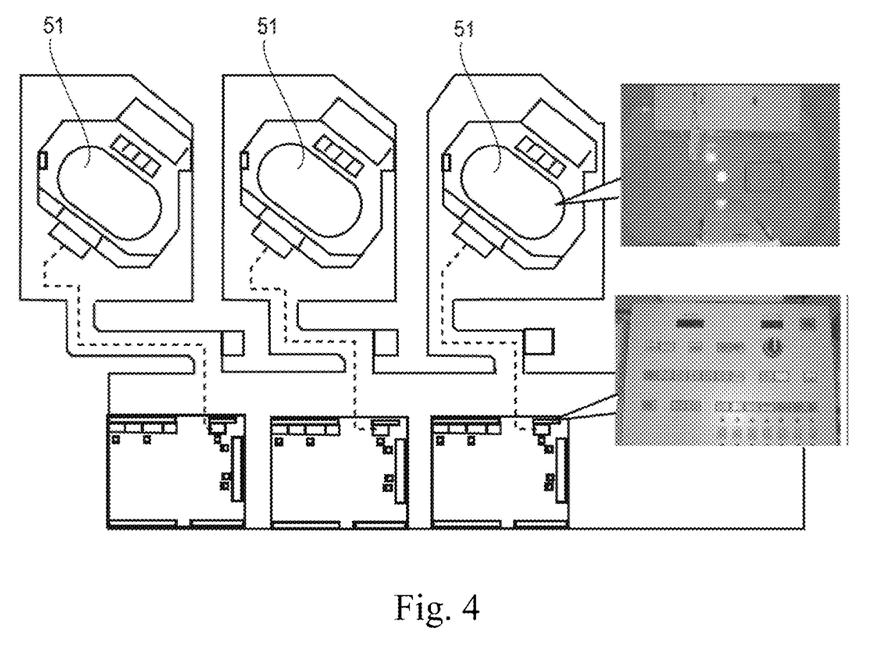
FIG. 4 is a design drawing of the device for remotely multi-portal irradiation of particle beams.

The device for remotely multi-portal irradiation of particle beams was actually designed. FIG. 4 is a design drawing of the device for remotely multi-portal irradiation of particle beams. In the device for remotely multi-portal irradiation of particle beams, three irradiation rooms are present, and operation of three irradiation devices is controlled by controllers in control rooms, respectively. Each irradiation device and each irradiation control device are connected, by a conducting wire, to each controller. The medical staff can control each irradiation device and each irradiation control device by using the controller or the remote operation controller in the control room. Note that, in the example illustrated in FIG. 4, the control room and the controller corresponding to each particle beam irradiation device are present; however, a plurality of particle beam irradiation devices can also be controlled in one control room.

In the related art, there is provided, in the vicinity of a treatment bed, a handheld type operation device for use in a treatment room, and setting and operation of irradiation equipment are performed using the operation device. In the present invention, a remote controller for multi-portal irradiation that can perform the same operation as the handheld type operation device of the related art provided in the treatment room is installed in an operation room. When setting of the irradiation device is made, an operator operates the irradiation device while checking a patient monitoring camera monitor installed beside the remote controller. Furthermore, the shape of the multileaf collimator can be checked from the control room by using the MLC remote monitoring camera. In this manner, in the present example, the remotely multi-portal irradiation of particle beams can be achieved.

INDUSTRIAL APPLICABILITY

The present invention can be used in the field of medical equipment.

REFERENCE SIGNS LIST

11 Irradiation target
12 Irradiation device
13 Irradiation control device
14 Support stand
15 Irradiation room
17 Operation controller
18 MLC remote monitoring camera
21 Control room
22 Control device
24 Multileaf collimator
25 Mirror
31 Imaging device
32 X-ray photographing device
41 Remote operation controller
42 Display section
51 Rotating gantry

The invention claimed is:

1. A system for remotely controlling multi-portal irradiation of particle beams, the system comprising:
   an irradiation room including an irradiation device that emits a particle beam to an irradiation target, an irradiation control device that controls a position and direction of the irradiation device, and a support stand that supports the irradiation target;
   a control device disposed in a control room which is separate from the irradiation room; and
   an imaging device that detects and images a positron which is generated from the irradiation target when it is irradiated with the particle beam emitted from the irradiation device,
   wherein:
   the control device controls the irradiation control device to control the position and direction of the irradiation device; and
   the irradiation room further includes a MLC remote monitoring camera configured for photographing a shape of a multileaf collimator in the irradiation device and displaying the multileaf collimator shape on a display section in the control room to allow an operator to check the multileaf collimator shape.

2. The system according to claim 1, wherein
   the control device stores information related to an irradiation field of the particle beam with which the irradiation target is irradiated from each position and direction of the irradiation device controlled by the irradiation control device, and allows the irradiation target to be irradiated with an adequate dose of the particle beam even when the irradiation device irradiates the irradiation target with the particle beam from a plurality of positions and directions.

3. The system according to claim 1, further comprising a X-ray photographing device that performs X-ray photographing of the irradiation target.

4. The system according to claim 1, wherein
   the control device has a remote operation controller configured for remotely controlling the irradiation control device.

5. The system according to claim 1, wherein the irradiation device and the irradiation control device are incorporated in a rotating gantry, or constitute a part of the rotating gantry.

6. The system according to claim 1, wherein the irradiation device includes a snout, and the multileaf collimator is disposed inside the snout.

7. The system according to claim 6, further comprising a bolus disposed inside the snout and configured to stop the particle beam at a depth corresponding to a shape of a bottom of an affected part of the irradiation target.

8. The system according to claim 1, wherein the control device further controls the support stand such that the support stand is configured to move up and down, right and left, and front and back based on a command from the control device.

* * * * *